United States Patent [19]
Davis et al.

[11] 3,983,874
[45] Oct. 5, 1976

[54] CATAMENIAL DIAPHRAGM WITH REPLACEABLE TAMPON

[76] Inventors: Alwyn K. Davis, 88 Pinecrest Drive, Thousand Oaks, Calif. 91360; Ward A. St. John, 3684 San Vicente Court, Newbury Park, Calif. 91320

[22] Filed: June 26, 1975

[21] Appl. No.: 590,459

[52] U.S. Cl. .................... 128/285; 128/127
[51] Int. Cl.² ............... A61F 5/46; A61F 13/20
[58] Field of Search ............ 128/285, 127–131, 128/270, 294

[56] References Cited
UNITED STATES PATENTS

| | | | |
|---|---|---|---|
| 2,020,107 | 11/1935 | Cruickshank | 128/271 |
| 2,423,356 | 7/1947 | Waterbury | 128/127 |
| 2,616,426 | 11/1952 | Gordon | 128/285 |
| 3,036,570 | 5/1962 | Milgrom et al. | 128/127 |
| 3,128,767 | 4/1964 | Nolan | 128/285 |
| 3,216,422 | 11/1965 | Steiger et al. | 128/285 |
| 3,683,904 | 8/1972 | Forster | 128/127 |

*Primary Examiner*—Aldrich F. Medbery

[57] ABSTRACT

A menses collector adapted to be used during coitus for the collection of uterine discharge at the cervix thereby to isolate the same in a pocket retaining absorbtive material and preventing the same from entering into the vaginal vault. A removeable cover of supple material is attached to a pliant diaphragm, there being a yieldable opening in the cover to seal with the cervix opening therethrough into said pocket, and there being a rim at the perimeter of the diaphragm to seal with the vaginal walls and stabilizing the device between the fornix and the pubis symphysis.

17 Claims, 4 Drawing Figures

CATAMENIAL DIAPHRAGM WITH REPLACEABLE TAMPON

BACKGROUND

This invention relates primarily to the collection of the menses in the human female, and secondarily to contraception if so desired. It is a general object to ensure against discharge of the menses while extending athletic and marital activities of the female without offensive affect. The female menstruation period causes a discharge of approximately 30–100cc of liquid through the portio vaginalis of the cervix, and it is this fluid that is to be intercepted and contained so as to be isolated and unnoticeable for physiological reasons involving aesthetic sensibility.

The female menses is not as voluminous as generally believed, as it is comingled with other body secretions when discharged from the vagina. In this respect, it is isolation of the discharge from the cervix which is an object of this invention, wherein the menses is collected at the cervix and prevented from discharging therefrom into the vagina. This placement of the collective device prevents the admixture of the menses with other body fluids and greatly reduces the sanitary problem.

Coitus as a human function is often desired of a female near or during the menstration period and to ensure against menstrual discharge is much to be desired, and it is to this end that a supple and pliable diaphragm is provided with a cover to form a sack for the containment of the menses, to go substantially unnoticed during intercourse. With the present invention, the cervix protrudes into this collection device where it discharges directly into an absorbtive tampon contained within an impervious membrane. There is a primary seal around the cervix and a secondary seal at the perimeter of the diaphragm.

Insertion of a diaphragm and its placement is to be considered, and in order to have the primary seal above referred to there is an opening located eccentrically in the pocketed device for the cervix, with a flexible rim of the diaphragm stiffened and stabilized in position between the posterior fornix and the symphysis thereby properly locating said opening. It is an object therefore, to provide such an opening and seal into the pocket of the device, whereby the menses is collected and contained within the pocket.

Containment of menses within a pocketed diaphragm of substantially unnoticeable character is an object herein, and which is accomplished by providing a saturable disc-shaped tampon retained within the diaphragm by a removeable cover, whereby the tampon is replaceable and the device per se reuseable. To this end the cover is forcibly removable from the rim of the diaphragm, capturing the tampon therein.

Removal of a saturated tampon is facilitated with this pocketed diaphragm having a cover for the retainment thereof. Assuming that the female body is erect or faced upwardly, the aforementioned opening for reception of the menses from the cervix will also be upwardly disposed as the device is withdrawn from the vaginal vault. In this respect it is an object to provide a catamenial device that presents a reservoir for the uterine discharge and with an expendible tampon retained therein to hold liquid without spillage during removal.

Convenience of a catamenial device is much to be desired and in this respect it is an object of this invention to provide a configuration that can be gripped for withdrawal thereof, and to provide means for quick removal and replacement of the cover which establishes the pocket. In practice, the permanent elements of this device are fabricated of elastomeric material that is supple and pliant, and which is adapted to be formed with an undercut channel in one part and into which a mating beaded part can be forcibly received, all without deep crevases and easily cleaned.

SUMMARY OF INVENTION

The menses collection device herein disclosed is a pocketed structure having an opening therein to seal with the vaginal walls at/or surrounding the cervix and removably carrying an absorbtive tampon. The device is similar to a diaphragm, in that it has a flexible rim supporting a pliable membrane. Additionally however, this menses collector has a supple cover with an opening therethrough to yield to the cervix which enters and discharges directly into said pocket. In the preferred form, the cover is a part separate from the diaphragm per se and adapted to be forcibly secured thereto coextensively around the rim. Characteristically, the opening is eccentrically related to the rim diameter so that the device will properly enter said opening when the rim of the diaphragm is captured in the posterior fornix, there being a perimeter rim for manipulation of the device into and out of stabilized position supported behind the symphysis. The pocket-like structure of this device establishes a sack-like vessel that presents a supple wall exposed anteriorly within the vaginal vault and backed by the absorbent tampon which is protectively housed and sealed off primarily at the cervix and secondarily at the diaphragm rim.

DRAWINGS

The various objects and features of this invention will be fully understood from the following detailed description of the typical preferred form and application thereof, throughout which description reference is made to the accompanying drawings, in which.

PREFERRED EMBODIMENT

Figure 1:
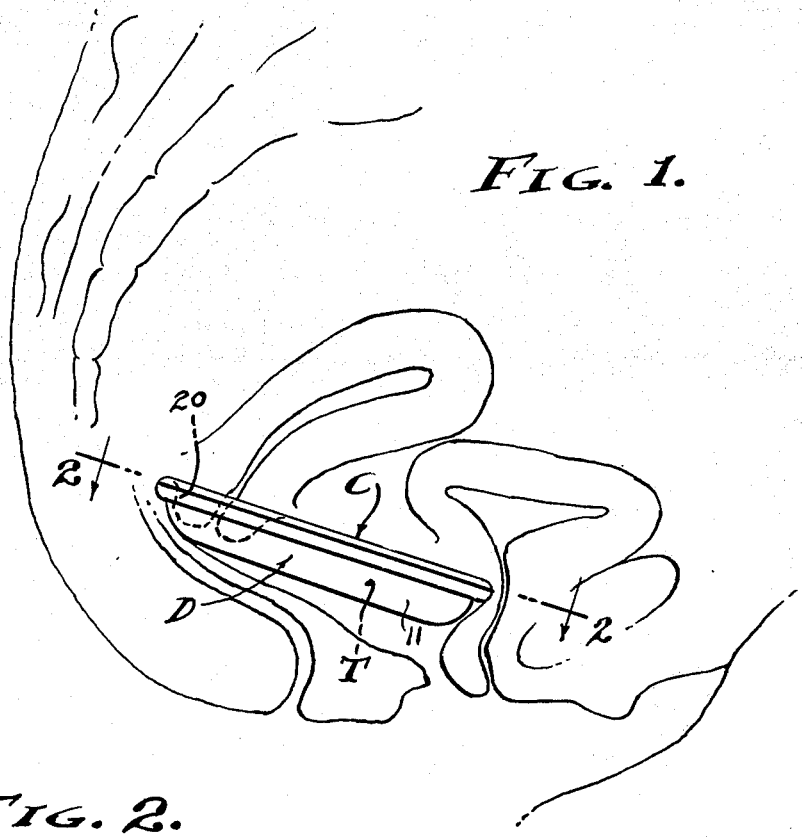
FIG. 1 is a cross sectional view of the female anatomy, showing a typical installation of the pocketed diaphragm of the present invention.

Referring now to the drawings, sealed placement of this catamenial diaphragm D is shown in FIG. 1, stabilized in position by its flexible rim R at the perimeter thereof, the diaphragm being characterized by a pliant posterior-bottom wall and all of which is commonplace in contraceptive diaphragms and the like. The rim R is reinforced by means of a circumferentially coextensive spring coil 10 weakened at diametrically opposite portions (not shown) so as to facilitate collapse for insertion into position in the vagina. The diaphragm per se then comprises a sack 11 that depends from and extends diametrically of the coil 10 and which is embedded in a protective rim 13. The rim diameter will vary between 70 to 110cm, to be prescribed for use with each individual person. Thus, a chambered space is established by the sack 11 below the plane of the rim 13. And, in accordance with this invention, the rim 13 carries a cover C in the plane thereof, thereby providing a pocket of chamber within the device. The diaphragm and cover can be an expendible unit integrally formed of supple and pliant elastic material within which a tampon T is inserted. However, it is preferred that the cover C be removable for facilitating replaceability of the tampon T and for cleansing. In practice, a continuous circumferential channel 15 of undercut configuration opens upwardly in the rim 13, this channel being characterized by convergent side walls in the integral body of supple and pliant elastomeric material.

The cover C is provided in accordance with this invention to establish the chamber and pocket configuration that forms a vessel for the retainment of the tampon T. As is suggested above, the cover C and diaphragm D can be integral providing that the material thereof is elastic enough to permit replaceability of the tampon T. However, it is preferred that the cover C be separate from the diaphragm D so as to facilitate replacement of the tampon and for cleaning of the permanent and reuseable elements C and D. Therefore, the cover C is a disc-shaped anterior-top element of supple material, having a pliable wall 16 and a downwardly disposed peripheral bead 17 complementary to the channel 15 in the diaphragm. Accordingly, the bead 17 is an enlargement having a divergency to mate with the convergency of the channel 15 and to the end that a forcible mating effect is achieved whereby the bead is held secured in the channel coextensively of the perimeter of the two elements C and D.

Figure 2:
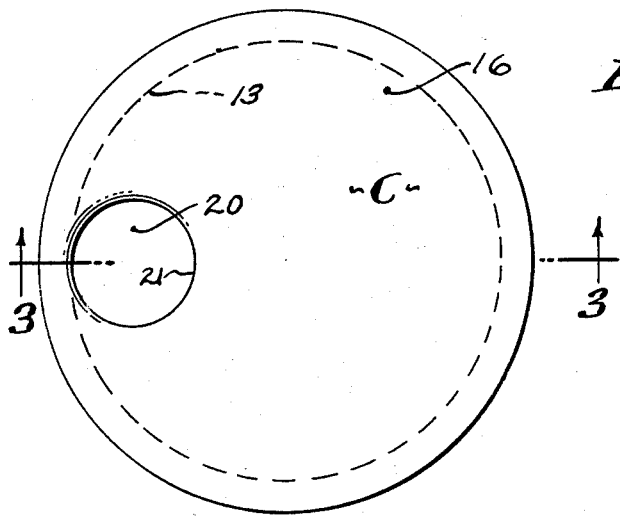
FIG. 2 is a top view of the device taken as indicated by line 2—2 on FIG. 1.
Figure 4:
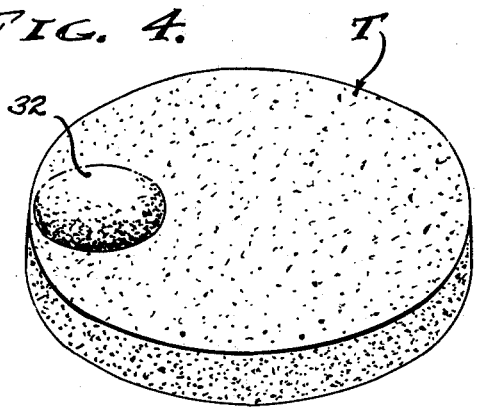
FIG. 4 is a perspective view of the absorbtive tampon that is removably carried in the pocket formed by the device.
Figure 3:
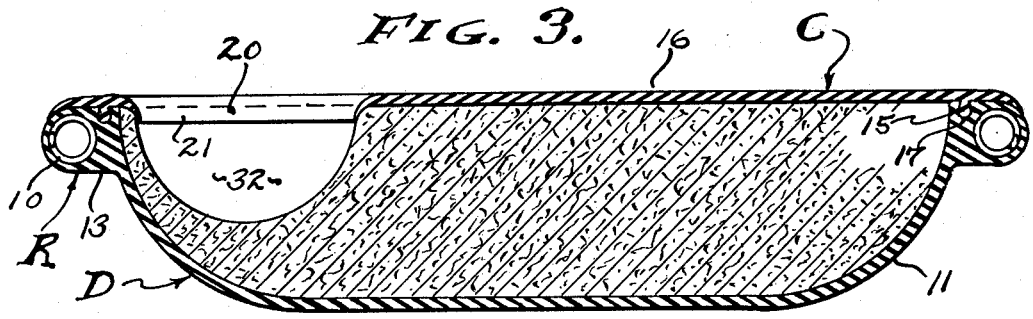
FIG. 3 is an enlarged longitudinal sectional view of the device taken as indicated by line 3—3 on FIG. 2.

In accordance with and a feature of the present invention is the provision of an opening 20 in the cover C, and with which the cervix seals and extends or protrudes through for discharge into the chamber. The opening 20 is normally 26mm to 32mm in diameter and varies according to the size and/or mean and effective diameter of the cervix as it protrudes into the vaginal vault. As best shown in FIG. 2, the opening 20 is circular and is eccentrically located adjacent and tangent to the rim 13 at one (the posterior) side of the cover and of the diaphragm. Thus, the channel and bead seal is continuous and uninterrupted, the rim 13 in the tangential area of the opening 20 is gradually narrowed so as to be held in the fornix posteriorly of the cervix thereby confined to project through said opening 20. in practice, the opening 20 is provided with an inturned lip 21 that engageably seals with the exterior surface of the convex cervix that partially or completely penetrates therethrough; and to this end the primary seal is established. The rim 13 and/or periphery of diaphragm D and overlying cover C attached thereto is provided with a toroidal exterior that engageably seals with the anterior wall of the vaginal vault surrounding the cervix; and to the end that the secondary seal is established.

In the event that this catamenial device is to be used for contraceptive purposes, a spermicidal preparation can be applied to the cover C at the aforementioned parimary and/or secondary seals.

The tampon T is provided to occupy the chamber and to restrict depression thereof, so that displacement of absorbed menses is maintained. Although a variety of materials can be employed for this purpose, compacted cotton fibers or the like are used which expand as they assimilate liquid therebetween by absorption.

As shown, the tampon T is a disc of compacted cellulous fibers, with bottom and top walls 30 and 31 juxtaposed to the diaphragm sack 11 and curved wall 16 respectively. In practice, there is a recess or peripheral depression 32 to accommodate entry of the cervix into the chamber otherwise occupied by the tampon T.

As a convenience for removal, the pliable wall 16 of the cover C is supple and readily depressible by a person's finger engaged over the rim 13, to be followed with a prehensile grip, partial collapse of the rim and subsequent removal of the device.

From the foregoing it will be seen that the catamenial device herein disclosed is unique with respect to the cover C and its combined relationship to the diaphragm D to be stabilized and thereby positioned to receive the cervix for penetration into the chamber thereof. A diaphragm D of certain diameter and a cover C with an opening 20 of certain diameter will be prescribed for the individual female, the insertion and removal thereof being as hereinabove described.

Having described only a typical preferred form and application of our invention, we do not wish to be limited or restricted to the specific details herein set forth, but wish to reserve to ourselves any modifications or variations that may appear to those skilled in the art:

We claim:

1. A catamenial device for the collection of uterine discharge from the cervix, and comprising in combination; a diaphragm of supple impervious material having a flexible rim defining its perimeter and a membraneous sack depending coextensively from the rim and forming a chamber below the plane of said rim, and a cover of supple impervious material carried by and in the plane of the said rim to close the chamber formed by the sack and having an eccentrically positioned opening therethrough to receive the protrusion of the cervix when the diaphragm is stabilized with its rim disposed between the posterior fornix and pubis symphysis.

2. The catamenial device as set forth in claim 1, wherein the said opening is adjacent and tangent to the rim of the diaphragm thereby to receive the protrusion of the cervix when the diaphragm is stabilized.

3. The catamenial device as set forth in claim 1, wherein the said opening in the cover is of a diameter to yield to protrusion of the cervix therethrough to seal therewith when the diaphragm is stabilized.

4. The catamenial device as set forth in claim 1, wherein the said opening in the cover has a lip to yieldingly engage around the protruding cervix and to seal therewith when the diaphragm is stabilized.

5. The catamenial device as set forth in claim 1, wherein the diaphragm rim supportably engages the cover adjacent to the opening to receive the protrusion of the cervix when the diaphragm is stabilized.

6. The catamenial device as set forth in claim 1, wherein the diaphragm rim supportably engages the cover adjacent to the opening and of a diameter to yield to protrusion of the cervix therethrough to seal therewith when the diaphragm is stabilized.

7. The catamenial device as set forth in claim 1, wherein the diaphragm rim supportably engages the cover adjacent to the opening to receive the cervix, and wherein the said opening in the cover has a lip to yieldingly engage around the protruding cervix and to seal therewith when the diaphragm is stabilized.

8. A catamenial device for the absorptive collection of uterine discharge from the cervix, and comprising in combination; a diaphragm of supple impervious material having a flexible rim defining its perimeter and a membraneous sack depending coextensively from the rim and forming a chamber below the plane of said rim, a disc-shaped tampon occupying said chamber, and a cover of supple impervious material carried by and in the plane of said rim to close and retain the tampon in the chamber formed by the sack and having an eccentrically positioned opening therethrough to receive the protrusion of the cervix for absorption of discharge into said tampon when the diaphragm is stabilized in position against the walls of the vaginal vault with its rim disposed between the posterior fornix and pubis symphysis.

9. The absorptive catamenial device as set forth in Claim 8, wherein the said opening is adjacent and tangent to the rim of the diaphragm thereby to receive the protrusion of the cervix for absorption of discharge into said tampon when the diaphragm is stabilized.

10. The absorptive catamenial device as set forth in Claim 8, wherein the said opening in the cover is of a diameter to yield to protrusion of the cervix therethrough to seal therewith for absorption of discharge of said tampon when the diaphragm is stabilized.

11. The absorptive catamenial device as set forth in Claim 8, wherein the said opening in the cover has a lip to yieldingly engage around the protruding cervix and to seal therewith for absorption of discharge into said tampon when the diaphragm is stabilized.

12. The absorptive catamenial device as set forth in claim 8, wherein the diaphragm rim supportably engages the cover adjacent to the opening to receive the protrusion of the cervix for absorption of discharge into said tampon when the diaphragm is stabilized.

13. The absorptive catamenial device as set forth in claim 8, wherein the diaphragm rim supportably engages the cover adjacent to the opening and of a diameter to yield to protrusion of the cervix therethrough to seal therewith for absorption of discharge into said tampon when the diaphragm is stabilized.

14. The absorptive catamenial device as set forth in claim 8, wherein the diaphragm rim supportably engages the cover adjacent to the opening to receive the cervix, and wherein the said opening in the cover has a lip to yieldably engage around the protruding cervix and to seal therewith for absorption of discharge into said tampon when the diaphragm is stabilized.

15. A catamenial device for the absorptive collection of uterine discharge from the cervix, and comprising in combination; a diaphragm of supple impervious material having a flexible rim defining its perimeter, a membraneous sack depending coextensively from the rim and forming a chamber below the plane of said rim, securement means coextensive of said rim, a disc-shaped tampon occupying said chamber, a cover of supple impervious material with a perimeter seal held coextensively to the diaphragm rim by the securement means and in the plane of the said rim to close and retain the tampon in the chamber formed by the sack and having an opening therethrough positioned to receive the protrusion of the cervix when the diaphragm is stabilized in position against the walls of the vaginal vault with its rim disposed between the posterior fornix and pubis symphysis.

16. The absorptive catamenial device as set forth in claim 15, wherein the securement means comprises a circumferentially continuous yieldable recess and bead engagement.

17. The absorptive catamenial device as set forth in claim 15, wherein the securement means comprises a yieldable circumferentially continuous channel and a forcible bead engagement.

\* \* \* \* \*